United States Patent [19]

Petzoldt et al.

[11] 4,029,779
[45] June 14, 1977

[54] 1α-HYDROXY STEROIDS

[75] Inventors: Karl Petzoldt; Walter Elger, both of Berlin, Germany

[73] Assignee: Schering Aktiengesellschaft, Berlin & Bergkamen, Germany

[22] Filed: Oct. 17, 1975

[21] Appl. No.: 623,542

[30] Foreign Application Priority Data

Oct. 18, 1974 Germany .................. 2450106
Sept. 1, 1975 Germany .................. 2539261

[52] U.S. Cl. .................. 424/243; 260/397.4; 195/51 S
[51] Int. Cl. .................. A61k 31/56; C07j 1/00
[58] Field of Search .................. 260/397.4; 424/243

[56] References Cited

UNITED STATES PATENTS

| | | | |
|---|---|---|---|
| 2,833,794 | 5/1958 | Goldkamp et al. | 260/397.4 |
| 3,294,646 | 12/1966 | Smith et al. | 195/51 |
| 3,565,778 | 2/1971 | Jeger et al. | 204/158 |

Primary Examiner—Elbert L. Roberts

Attorney, Agent, or Firm—Millen & White

[57] ABSTRACT

1α-Oxysteroid of the formula

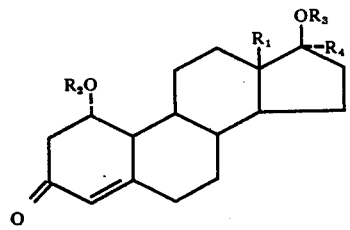

wherein
  $R_1$ is methyl or ethyl,
  $R_2$ and $R_3$ each are hydrogen or alkanoyl of 1–8 carbon atoms, and
  $R_4$ is hydrogen or hydrocarbon of 1–4 carbon atoms, are progestestionally active and useful in oral contraceptive and menopausal compositions.

8 Claims, No Drawings

1α-HYDROXY STEROIDS

BACKGROUND OF THE INVENTION

This invention relates to novel, pharmacologically active 1α-oxy steroids, to a process for the preparation thereof, and to medicinal agents containing these compounds.

DETAILED DESCRIPTION

The novel 1α-hydroxy steroids and their esters are characterized by the general Formula I

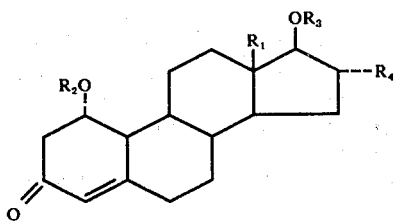

wherein
$R_1$ is a methyl group or ethyl,
$R_2$ and $R_3$ each are hydrogen or alkanoyl of 1–8 carbon atoms, and
$R_4$ is a hydrogen or hydrocarbon of 1–4 carbon atoms.

According to the invention, the $R_2$ and $R_3$ are hydrogen or alkanoyl of 1–8 carbon atoms which can be alike or different from each other. Suitable alkanoyl groups $R_2$ and $R_3$ include, for example, formyl, acetyl, propionyl, butyryl, isobutyryl, pentanoyl, isovaleroyl, hexanoyl, heptanoyl, and octanoyl groups. Of these, acetyl and heptanoyl are especially preferred.

Hydrocarbon $R_4$ groups at the 17α-position are alkyl, alkenyl or alkynyl of up to 4 carbon atoms. Typical $R_4$ hydrocarbon groups include methyl, ethyl, vinyl and ethynyl. However, the unsaturated groups including vinyl and, especially, ethynyl are preferred.

Of the novel compounds of this invention, the most preferred are those of Formula I wherein $R_4$ is ethynyl. A group of compounds which are particularly preferred are those of Formula I wherein $R_1$ is methyl and $R_4$ is ethynyl. An equally preferred series of compounds are those of Formula I wherein $R_1$ is ethyl and $R_4$ is ethynyl.

The 1α-oxysteroids of this invention are prepared by fermenting a compound of Formula II

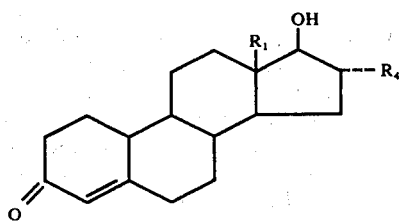

wherein $R_1$ and $R_4$ have the above-indicated meanings, with a fungal culture of the genera Rhizoctonia, Calonectria, Glomerella, Aspergillus, Corticium, Septomyxa, Mucor, Isaria, Irpex, or Fusarium, and by optionally esterifying the hydroxy groups.

The process of this invention can be conducted, for example, with the use of the following strains of fungi:

| | |
|---|---|
| Rhizoctonia solani | (ATCC 10154) |
| Glomerella glycines | (ATCC 11871) |
| Glomerella fusaroides | (ATCC 9552) |
| Calonectria decora | (ATCC 14767) |
| Aspergillus clavatus | (ATCC 9598) |
| Aspergillus fumigatus mut. helvola | (CBS 11046) |
| Aspergillus carneus | (CBS 49465) |
| Aspergillus terreus | (ATCC 10020) |
| Aspergillus conicus | (IFO 4047) |
| Corticium sasakii | (Univ. Tokyo 9005) |
| Septomyxa affinis | (ATCC 6737) |
| Mucor griseocyanus | (ATCC 1207b) |
| Mucor genevensis | (ATCC 8976) |
| Mucor spinosus | (CBS 29563) |
| Isaria farinosa | (OUT 4098) |
| Irpex lacteus | (IFO 5367) |
| Fusarium ciliatum | (CBS 13235) |

Most preferably are Calonectria decora, Aspergillus clavatus, and Mucor spinosus.

The hydroxylation is accomplished according to methods as usually employed for the microbiological hydroxylation of steroids with fungal cultures.

Thus, optimum fermentation conditions are determined analytically, generally by thin-layer chromatography, in preliminary experiments, such as, for example, the selection of the most advantageous nutrient medium, the suitable subtrate solvent, the substrate concentration, the operating conditions, e.g. temperature, aeration, pH, optimum time periods for germination, addition of substrate, and substrate contact on the enzyme of the microorganism.

Concentrations of about 50–1000 mg. of substrate per liter of nutrient medium are preferably used. The pH is preferably adjusted in the range of 5–7. The incubation temperature can range between 20° and 40° C., but preferably is 25°–35° C. For purposes of aeration, approximately 1 liter of air is introduced per minute per liter of the culture broth. The conversion of the substrate is suitably followed and controlled by the analysis of sample extracts by thin-layer chromatography. In general, reasonable amounts of hydroxylated steroid have been formed after 20–120 hours.

In the microbiological hydroxylation, the isomeric 1β-hydroxy steroids are also frequently formed in addition to the 1α-hydroxy steroids of general Formula I of this invention.

The products of the process are isolated and purified in a conventional manner. For example, the products of the process can be extracted with an organic solvent, such as methyl isobutyl ketone; the extract can be evaporated; and the products can be separated and purified by column chromatography.

Using the process of this invention, the following 1α,17β-dihydroxy steroids of general Formula I can be prepared, for example:

1α,17β-dihydroxy-4-estren-3-one,
1α,17β-dihydroxy-18-methyl-4-estren-3-one,
1α,17β-dihydroxy-17α-methyl-4-estren-3-one,
1α,17β-dihydroxy-17α,18-dimethyl-4-estren-3-one,
1α,17β-dihydroxy-17α-ethynyl-4-estren-3-one, and
1α,17β-dihydroxy-18-methyl-17α-ethynyl-4-estren-3-one.

The optional esterification of the free hydroxy groups is done according to the methods customarily used in steroid chemistry for the esterification of secondary and tertiary hydroxy groups. An example of a suitable esterification method is the reaction of the steroid with an acid anhydride or an acid chloride in the presence of a basic catalyst, such as sodium bicarbonate, potassium bicarbonate, potassium carbonate, sodium hydroxide, potassium hydroxide, pyridine, lutidine, collidine, or 4-dimethylaminopyridine.

The novel 1α-hydroxy steroids of general Formula I are pharmacologically active compounds. They exhibit a spectrum of activity similar to precursor steroids not hydroxylated in the 1-position, i.e., the novel compounds have a very high progestational activity, but, the androgenic side effect is markedly diminished in comparison to compounds not hydroxylated at the 1-position. Moreover, the compounds of this invention have estrogenic activity. On the basis of this unusual combination of properties, the novel compounds are very valuable active agents.

For therapeutic usage, the novel compounds are processed by the customary medicine procedures using the additives, vehicles, and flavor-ameliorating agents customary in galenic pharmacy in accordance with conventional methods. Pharmaceutically acceptable organic or inorganic carrier substances suitable for parenteral, enteral or topical application and which do not deleteriously react with the active compounds include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers coloring, flavoring and/or aromatic substances and the like which do not deleteriously react with the active compounds.

Suitable for oral administration are tablets, dragees, capsules or pills having talc and/or a carbohydrate carrier or binder or the like, the carrier preferably being lactose and/or corn starch and/or potato starch. A syrup, elixir solution or suspension or the like can be used wherein a sweetened vehicle is employed. Sustained release compositions can be formulated including those wherein the active compound is protected with differentially degradable coatings, e.g., by micro-encapsulation, multiple coatings, etc.

For parenteral application oily solutions, e.g., sesame oil and castor oil solutions, which can optionally contain furthermore a diluent, e.g., benzyl benzoate or benzyl alcohol, are preferred. Suspensions, emulsions or implants, including suppositories can also be used.

The concentration of an active agent in the thusformulated medicinal agents is dependent on the form of administration, the specific compound being utilized, the particular compositions formulated, and the particular situs and condition being treated. Optimal application rates for a given set of conditions can be ascertained by those skilled in the art using conventional dosage determination tests in view of the above guidelines.

Generally, however, the compounds of this invention are dispensed in unit dosage form comprising 50-200 mg. of a pharmaceutical carrier per each unit dosage and a progestationally effective amount of active agent of the invention per unit dosage of about 0.1 to 2 mg.

The novel medicinal agents are suitable as oral contraceptives; for therapy in connection with irregular menstrual cycles, and as menopausal preparations. They can be used as oral contraceptives also without an addition of estrogens. Of course, it is also possible to employ combinations of the novel progestogens with conventional estrogens.

The compounds of this invention are generally administered to mammals, e.g., human females. An effective daily dosage of the active compounds as administered orally or parenterally to human females generally comprises about 0.001 to 0.2, preferably 0.002 to 0.1 mg/kg. The dose can be administered singly or as divided dosages throughout the day.

Oral administration is preferred, the compounds of this invention being particularly valuable in the treatment of human females afflicted with irregular menstrual cycles or menopausal symptoms or of human females desirous of preventing pregnancy in an amount effective to adjust irregular cycles, alleviate menopausal symptoms or prevent pregnancy. In this regard, they can be employed in substantially the same manner as the known compound 17α-Ethynyl-17β-hydroxy-18-methyl-4-estren-3-one.

The following examples serve to explain the process of this invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

A 2-liter Erlenmeyer flask containing 500 ml. of a nutrient solution, sterilized in an autoclave for 30 minutes at 120° C., consisting of 5% glucose, 0.5% corn steep liquor, 0.2% sodium nitrate, 0.1% potasssim dihydrogen phosphate, 0.05% potassium chloride, 0.05% magnesium sulfate, and 0.002% iron(II) sulfate, is inoculated with a lyophilized culture of Calonectria decora (ATCC 14767) and shaken for 5 days at 30° C. on a rotary vibrator. By means of this subculture, a 20-liter fermentor, filled with 15 liters of a medium having the same composition as the subculture and sterilized at 121° C. and under 1.1 atmospheres gauge, is then inoculated. With the addition of "Silicone SH" as the defrother, the culture is incubated at 29° C. under aeration and agitation for 24 hours. One liter of the culture broth is transferred under sterile conditions into 14 liters of a nutrient medium sterilized as above and having the same composition; this culture is grown under the same conditions. After 12 hours, a solution of 7.5 g. of 17β-hydroxy-17α-ethynyl-4-estren-3-one in 75 ml. of dimethylformamide, filtered uner aseptic conditions, is added thereto and the mixture is further incubated.

After the substrate employed has been completely converted (38 hours' contact time), the content of the fermentor is extracted twice with 10 liters of methyl isobutyl ketone, and the extract is evaporated under vacuum at a bath temperature of 50° C. The remainder is washed repeatedly with hexane to remove the defrother, and is finally chromatographed over a silica gel column with the gradient methylene chloride - methylene chloride/acetone 8+2. Crystallization from acetone/isopropyl ether yields 1α,17β-dihydroxy-17α-ethynyl-4-estren-3-one, m.p. 207°–208° C.

EXAMPLE 2

100 mg. of 1α,17β-dihydroxy-17β-ethynyl-4-estren-3-one is combined with 3 ml. of pyridine and 0.3 ml. of acetic anhydride and agitated for 20 hours at 30°–35° C. The mixture is concentrated under a high vacuum, the residue is taken up in ethyl acetate, the ethyl acetate phase is washed, dried, concentrated under vacuum; the product is 17 - hydroxy-1α-acetoxy-17β-ethynyl-4-estren-3-one as a colorless oil.

EXAMPLE 3

A 2-liter Erlenmeyer flask containing 500 ml. of a nutrient solution sterilized for 30 minutes at 120° C. in an autoclave and consisting of 3.0% glucose, 1.0% corn steep, 0.2% NaNO₃, 0.1% KH₂PO₄, 0.2% K₂HPO₄, 0.05% MgSO₄, 0.002% FeSO₄, and 0.05% KCl is inoculated with a lyophilized culture of the strain Aspergillus clavatus (ATCC 9598) and grown for 2 days at 30° C. on a rotary shaker. By means of this subculture, a 50-liter fermentor filled with 30 liters of a medium having the same composition as the subculture and sterilized at 121° C. and under 1.1 atm. gauge is inoculated. With the addition of Silicone SH as the defrother, the culture is germinated at 29° C. under aeration and agitation for 72 hours.

900 ml. of the culture broth is transferred under sterile conditions into 14 liters of a nutrient medium sterilized as above and having the same composition and incubated under the same conditions. After 24 hours, a sterilized suspension of 7.5 g. of 17α-ethynyl-17β-hydroxy-18-methyl-4-estren-3-one in distilled water, extremely finely ground in the presence of aqueous "Tween" 80, polyoxyethylene ether of sorbitol mixed esters, is added to the reaction mixture and the germination is continued.

The progress of the conversion is observed by analyzing the methyl isobutyl ketone extracts of fermentor samples by thin-layer chromatography. After a contact time of about 90 hours, the conversion is complete. The fungal mycelium is filtered off, and the culture filtrate is extracted twice with respectively 10 liters of methyl isobutyl ketone. In a parallel procedure, the filtered-off mycelium is agitated repeatedly with a mixture of methyl isobutyl ketone, acetone, and water, thus being extracted.

The organic extract solutions are combined and evaporated to dryness under vacuum at a bath temperature of 50° C. The remaining residue is washed several times with hexane and finally chromatographed over a silica gel column. For purposes of further purification, the product is crystallized from methylene chloride/benzene, and the benzene solvate is once more precipitated from ethanol/water to remove the benzene. The pure 17α-ethynyl-1α,17β-dihydroxy-18-methyl-4-estren-3-one melts at 180° C.

EXAMPLE 4

500 mg. of 17α-ethynyl-1α,17β-dihydroxy-18-methyl-4-estren-3-one is dissolved in 10 ml. of pyridine; 0.5 ml. of acetic anhydride is added to the solution and the latter is allowed to stand for 30 hours in a refrigerator. To complete the reaction, the mixture is then agitated for several hours at room temperature. The reaction mixture is then evaporated under a high vacuum, the residue is taken up in ethyl acetate and washed neutral with distilled water. After drying over sodium sulfate and concentration of the ethyl acetate solution, 1α-acetoxy-17α-ethynyl-17β-hydroxy-18-methyl-4-estren-3-one is obtained.

EXAMPLE 5

650 mg. of 17α-ethynyl-1α,17β-dihydroxy-18-methyl-4-estren-3-one is taken up in 15 ml. of pyridine; 2 ml. of enanthic acid anhydride is added thereto and the mixture stirred for 16 hours at room temperature. The mixture is thereafter concentrated under high vacuum, the remainder is taken up in ethyl acetate and washed neutral with distilled water. Concentration of the dried ethyl acetate phase yields 17α-ethynyl-1α-heptanoyloxy-17β-hydroxy-18-methyl-4-estren-3-one as a slightly yellowish oil.

EXAMPLE 6

300 mg. of 17α-ethynyl-1α,17β-dihydroxy-4-estren-3-one is combined with 10 ml. of pyridine and 1.5 ml. of acetic anhydride and agitated under nitrogen for 4 days at room temperature. The reaction mixture is then evaporated under a high vacuum, the residue is taken up in ethyl acetate and washed neutral with distilled water. After drying over sodium sulfate and concentrating the ethyl acetate solution under vacuum, 17α-ethynyl-1α,17βdiacetoxy-4-estren-3-one is obtained.

Analogously, 17α-ethynyl-1α,17β-diacetoxy-18-methyl-4-estren-3-one is produced from 17α-ethynyl-1α,17β-dihydroxy-18-methyl-4-estren-3-one.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1α-oxy steroid of the formula

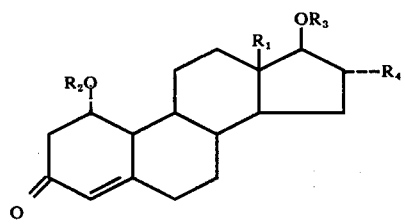

wherein R₁ is ethyl; R₂ and R₃ each are hydrogen atoms or alkanoyl of 1–8 carbon atoms; and R₄ is a hydrogen atom or hydrocarbon of 1–4 carbon atoms.

2. A compound of claim 1 wherein R₄ is ethynyl.
3. 17α-Ethynyl-1α,17β-dihydroxy-18-methyl-4-estren-3-one, a compound of claim 1.
4. 1α-Acetoxy-17α-ethynyl-17β-hydroxy-18-methyl-4-estren-3-one, a compound of claim 1.
5. 17α-Ethynyl-1α-heptanoyloxy-17β-hydroxy-18-methyl-4-estren-3-one, a compound of claim 1.
6. 17α-Ethynyl-1α,17β-diacetoxy-18-methyl-4-estren-3-one, a compound of claim 1.
7. A pharmaceutical composition comprising, in unit dosage form, a progestationally effective amount of a compound of claim 1 in admixture with a pharmaceutically acceptable carrier.
8. A method of treatment which comprises administering to a female having an irregular menstrual cycle or menopausal symptoms or to a fertile female for the prevention of pregnancy an amount effective to correct the irregular menstrual sycles, to alleviate the menopausal symptoms or to prevent pregnancy, respectively, of a 1α-oxy steroid of the formula
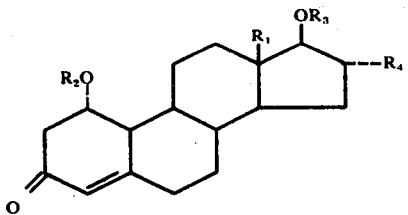
wherein $R_1$ is methyl or ethyl; $R_2$ and $R_3$ each are hydrogen atoms or alkanoyl of 1–8 carbon atoms; and $R_4$ is a hydrogen atom or hydrocarbon of 1–4 carbon atoms.
* * * * *

UNITED STATES PATENT AND TRADEMARK OFFICE
CERTIFICATE OF CORRECTION

PATENT NO. : 4,029,779            Page 1 of 2

DATED : June 14, 1977

INVENTOR(S) : KARL PETZOLDT ET AL.

It is certified that error appears in the above-identified patent and that said Letters Patent are hereby corrected as shown below:

Column 1, lines 14-23;

Column 6, Claim 1, lines 40-49;

Column 7, Claim 8, lines 6-15;

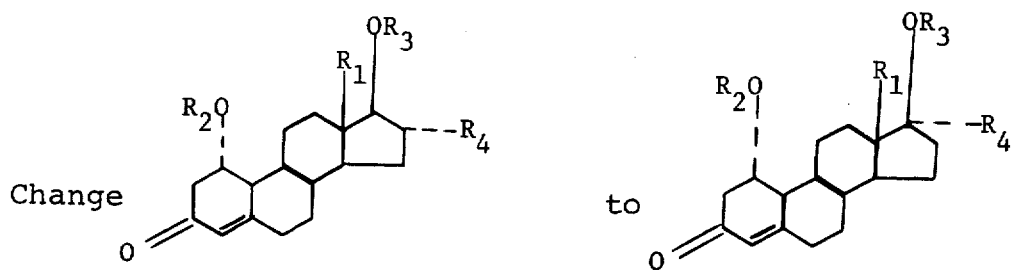

UNITED STATES PATENT AND TRADEMARK OFFICE
CERTIFICATE OF CORRECTION

PATENT NO. : 4,029,779

DATED : June 14, 1977

INVENTOR(S) : KARL PETZOLDT ET AL.

It is certified that error appears in the above-identified patent and that said Letters Patent are hereby corrected as shown below:

Column 1, lines 51-59;

Change 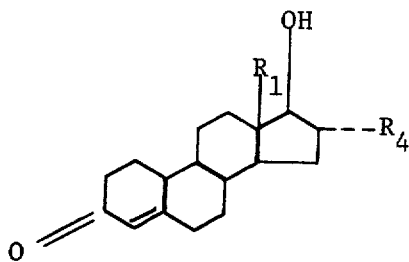 to 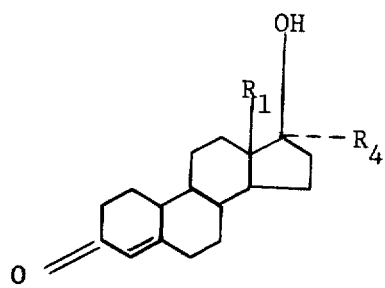

Signed and Sealed this

Fourteenth Day of February 1978

[SEAL]

Attest:

RUTH C. MASON
*Attesting Officer*

LUTRELLE F. PARKER
*Acting Commissioner of Patents and Trademarks*